United States Patent
Al-Buraik (10) Patent No.: US 11,079,358 B2
(45) Date of Patent: Aug. 3, 2021

(54) REMOTELY ASSESSING REAL-TIME WOODEN POLE INTEGRITY

(71) Applicant: Saudi Arabian Oil Company, Dhahran (SA)

(72) Inventor: Khaled A. Al-Buraik, Doha (SA)

(73) Assignee: Saudi Arabian Oil Company, Dhahran (SA)

( * ) Notice: Subject to any disclaimer, the term of this patent is extended or adjusted under 35 U.S.C. 154(b) by 252 days.

(21) Appl. No.: 16/394,553

(22) Filed: Apr. 25, 2019

(65) Prior Publication Data

US 2020/0340951 A1    Oct. 29, 2020

(51) Int. Cl.
  *G01N 29/07*    (2006.01)
  *G01N 29/11*    (2006.01)
  (Continued)

(52) U.S. Cl.
  CPC .............. *G01N 29/07* (2013.01); *G01N 29/11* (2013.01); *G01N 29/30* (2013.01); *G01N 29/348* (2013.01);
  (Continued)

(58) Field of Classification Search
  CPC ...... G01N 29/07; G01N 29/348; G01N 29/30; G01N 29/11; G01N 29/12; G01N 29/4427;
  (Continued)

(56) References Cited

U.S. PATENT DOCUMENTS

| 3,531,983 A | * | 10/1970 | Heath | .................. | G01N 29/045 |
| | | | | | 73/584 |
| 4,059,988 A | * | 11/1977 | Shaw | .................. | G01N 29/045 |
| | | | | | 73/579 |

(Continued)

FOREIGN PATENT DOCUMENTS

| JP | 61035349 A | * | 2/1986 | ............. G01N 29/07 |
| RU | 2272282 | | 1/2006 | |

(Continued)

OTHER PUBLICATIONS

Benoit and Sandoz, "New Wooden Poles Grading Using Non-Destructive Technology," Cired, 21st International Conference on Electricity Distribution, Frankfurt, Jun. 6-9, 2011, 4 pages.

(Continued)

*Primary Examiner* — David L Singer
(74) *Attorney, Agent, or Firm* — Fish & Richardson P.C.

(57) ABSTRACT

Methods and systems, including computer-implemented methods, computer program products, and computer systems for wooden pole integrity assessment. One computer-implemented method includes emitting, by one or more acoustic sources mounted onto a wooden pole, one or more sound waves through the wooden pole. Further, the method includes measuring, by one or more acoustic receivers mounted on the wooden pole, a respective amplitude and time of arrival of at least a portion of each of the one or more sound waves. Additionally, the method includes calculating, using the respective amplitude, the respective time of (Continued)

arrival, and a predetermined function, the real-time integrity level of the wooden pole. The method also includes in response to determining that the real-time integrity level of the wooden pole is less than a threshold level, outputting an alert indicating that the integrity level of the wooden pole is less than the threshold level.

18 Claims, 5 Drawing Sheets

(51) Int. Cl.
  *G01N 29/30*    (2006.01)
  *G01N 29/34*    (2006.01)
  *G01N 29/12*    (2006.01)
  *G01N 29/24*    (2006.01)
(52) U.S. Cl.
  CPC ......... *G01N 29/12* (2013.01); *G01N 29/2437* (2013.01); *G01N 2291/011* (2013.01); *G01N 2291/015* (2013.01); *G01N 2291/0238* (2013.01); *G01N 2291/0258* (2013.01); *G01N 2291/0289* (2013.01); *G01N 2291/02827* (2013.01); *G01N 2291/048* (2013.01); *G01N 2291/2634* (2013.01)
(58) Field of Classification Search
  CPC ....... G01N 2291/015; G01N 2291/011; G01N 2291/2634; G01N 2291/0289; G01N 2291/048; G01N 2291/0258; G01N 2291/0238; G01N 2291/02827; G01N 33/46
  See application file for complete search history.

(56) References Cited

U.S. PATENT DOCUMENTS

| | | | | |
|---|---|---|---|---|
| 4,350,044 A * | 9/1982 | Richardson | ............ | G01N 33/46 73/600 |
| 4,838,085 A * | 6/1989 | Pellerin | ................ | G01N 29/045 73/597 |
| 4,926,691 A * | 5/1990 | Franklin | ................ | G01H 13/00 703/2 |
| 5,024,091 A * | 6/1991 | Pellerin | .................... | G01N 3/30 73/597 |
| 5,237,870 A * | 8/1993 | Fry | ........................... | G01N 3/20 73/588 |
| 5,396,799 A * | 3/1995 | Ross | ...................... | E02D 33/00 73/579 |
| 5,621,172 A * | 4/1997 | Wilson | .................. | G01M 5/005 73/579 |
| 5,760,308 A * | 6/1998 | Beall | ...................... | G01N 29/07 73/598 |
| 6,029,522 A * | 2/2000 | Schafer | .............. | G01N 29/2493 73/587 |
| 6,092,418 A * | 7/2000 | Schafer | .............. | G01N 29/2493 73/597 |
| 6,276,209 B1 * | 8/2001 | Schafer | .................. | G01N 29/07 73/597 |
| 6,347,551 B1 * | 2/2002 | Turpening | ......... | G01N 29/0609 73/597 |
| 6,367,330 B1 * | 4/2002 | Schafer | .................. | G01N 29/30 73/597 |
| 2002/0109622 A1 * | 8/2002 | Miceli | ..................... | G01S 7/412 342/22 |
| 2009/0188320 A1 | 7/2009 | Greenough et al. | | |
| 2010/0295672 A1 * | 11/2010 | Hyland | .................... | H04Q 9/00 340/539.1 |
| 2014/0069192 A1 | 3/2014 | Bartuli et al. | | |
| 2014/0165731 A1 * | 6/2014 | Linford | .................. | G01N 29/46 73/592 |
| 2014/0278150 A1 * | 9/2014 | Baesler | ................... | E04H 12/00 702/34 |
| 2015/0355144 A1 * | 12/2015 | Bartuli | .................... | G01N 29/12 73/579 |
| 2018/0143237 A1 * | 5/2018 | Beaudet | .................. | H04Q 9/02 |
| 2018/0348169 A1 * | 12/2018 | Lee | ..................... | G01N 29/0672 |
| 2020/0088711 A1 * | 3/2020 | More | ..................... | G01N 21/95 |
| 2020/0370323 A1 * | 11/2020 | Pham | ................... | G08B 21/182 |

FOREIGN PATENT DOCUMENTS

| | | |
|---|---|---|
| WO | 01/65253 | 9/2001 |
| WO | 2017125730 | 7/2017 |

OTHER PUBLICATIONS

Sandoz and Benoit, "Timber grading machine using ultrasonic and density measurements: Triomatic," 2008, 8 pages.
Nelson, "Reliability-centered power line management inspection process, measurement techniques and data management considerations," The Institute of Electrical Engineers, May 1998, 24 pages.
PCT International Search Report and Written Opinion in International Appln. No. PCT/US2020/029321, dated Jul. 3, 2020, 15 pages.

* cited by examiner

FIG. 1

|  | Amplitude time<br>R1<br>a/t | Amplitude time<br>R2<br>a/t | Amplitude time<br>R3<br>a/t | Amplitude time<br>R4<br>a/t |
|---|---|---|---|---|
| $P_i$ (new) | | | | |
| $P_i$ (1) | | | | |
| $P_i$ (2) | | | | |
| $P_i$ (3) | | | | |

REMOTELY ASSESSING REAL-TIME WOODEN POLE INTEGRITY

TECHNICAL FIELD

This disclosure relates to a system that improves the reliability of transmission systems that utilize wooden utility poles.

BACKGROUND

For many years, wooden utility poles have been an integral part of transmission systems, such as power transmission systems. In transmission systems, wooden poles physically support devices and equipment that are used to transmit or carry signals (for example, electrical energy). The devices and equipment include transmission lines, transmitters, receivers, and antennas. For example, wooden poles in power transmission systems support transformers and overhead power lines (for example, subtransmission lines and distribution lines).

Given that wooden poles support integral elements of transmission systems, the failure of a wooden pole can have catastrophic consequences for a transmission system. For example, when a wooden pole of a power transmission system collapses, a significant portion of the power transmission system may be forced offline until the wooden pole is replaced. Given the time it takes to fix the pole, particularly when the pole is located in a remote location, the system may be offline for an extended period. In order to avoid scenarios where a wooden pole failure catastrophically affects a transmission system, transmission system operators attempt to predict when a wooden pole will fail. Doing so allows the operators to perform a maintenance operation on the wooden pole before it fails.

SUMMARY

The present disclosure describes methods and systems, including computer-implemented methods, computer program products, and computer systems for assessing the integrity of wooden poles. One computer-implemented method includes emitting, by one or more acoustic sources mounted onto the wooden pole, one or more sound waves through the wooden pole; measuring, by one or more acoustic receivers mounted on the wooden pole, a respective amplitude and time of arrival of at least a portion of each of the one or more sound waves; calculating, using the respective amplitude, the respective time of arrival, and a predetermined function, the real-time integrity level of the wooden pole; and in response to determining that the real-time integrity level of the wooden pole is less than a threshold level, outputting an alert indicating that the integrity level of the wooden pole is less than the threshold level.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware, installed on the system that in operation causes the system to perform the actions. One or more computer programs can be configured to perform particular operations or actions by virtue of including instructions that when executed by data processing apparatus cause the apparatus to perform the actions.

The foregoing and other implementations can each, optionally, include one or more of the following features, alone or in combination:

A first aspect, combinable with the general implementation, of periodically performing steps from emitting through outputting to periodically determine the real-time integrity level of the wooden pole.

A second aspect, combinable with any of the previous aspects, where the one or more acoustic sources are ultrasonic excitation devices, the one or more sound waves are ultrasonic sound waves, and the one or more acoustic receivers are piezoelectric transducer devices.

A third aspect, combinable with any of the previous aspects, where the one or more sound waves are sinusoidal 22-kilohertz (kHz) waves.

A fourth aspect, combinable with any of the previous aspects, where the one or more acoustic sources and the one or more acoustic receivers are powered by a power supply unit comprising a solar panel.

A fifth aspect, combinable with any of the previous aspects, where the predetermined function is generated by installing (i) respective first and second calibration acoustic sources, and (ii) respective calibration acoustic receivers on a plurality of calibration wooden poles; for each calibration wooden pole: emitting, by the respective first calibration acoustic source, a first calibration sound wave through the calibration wooden pole; measuring, by the respective acoustic receivers, an amplitude and an arrival time of the first calibration sound wave; emitting, by the respective second calibration acoustic source, a second calibration sound wave through the calibration wooden pole; and measuring, by the respective acoustic receivers, an amplitude and an arrival time of the second calibration sound wave; and based on (i) the amplitude and arrival time of the first calibration sound wave of each calibration wooden pole, (ii) the amplitude and arrival time of the second calibration sound wave of each calibration wooden pole, and (iii) a statistical model, generating the predetermined function to calculate a pole integrity based on arrival time and amplitude of sound waves.

A sixth aspect, combinable with any of the previous aspects, where the plurality of calibration wooden poles comprise a new wooden pole, and where the plurality of calibration wooden poles other than the new wooden pole are pre-damaged wooden poles with known respective pole integrities.

A seventh aspect, combinable with any of the previous aspects, where the statistical model is least square regression.

Particular implementations of the subject matter described in this specification can be implemented in order to improve the reliability of transmission systems that utilize wooden utility poles.

While generally described as computer-implemented software embodied on tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the following description. Other features and advantages of the disclosure will be apparent from the description and drawings, and from the claims.

BRIEF DESCRIPTION OF THE DRAWINGS

Like reference numbers and designations in the various drawings indicate like elements.

DETAILED DESCRIPTION

The following detailed description describes methods and systems that improve the stability and reliability of transmission systems that utilize utility poles, and is presented to enable a person skilled in the art to make and use the disclosed subject matter in the context of one or more particular implementations. Various modifications, alterations, and permutations of the disclosed implementations can be made and will be readily apparent to those skilled in the art, and the general principles defined may be applied to other implementations and applications without departing from the scope of the disclosure. Thus, the present disclosure is not intended to be limited to the described or illustrated implementations, but is to be accorded the widest scope consistent with the principles and features disclosed.

In line with the discussion above, transmission system operators attempt to predict a failure date of a wooden pole in order to replace the wooden pole before that date. Some operators rely on predictions methods that use known information about the wooden pole, such as the pole's wood type and an amount of time that the pole has been used. However, such methods do not account for many of the factors that have uniquely affected the integrity of that wooden pole. For example, the methods do not account for weather related damage sustained by the wooden pole, the growing conditions of the tree(s) used to manufacture the pole, and the weight of equipment supported by the pole, among other factors.

Disclosed herein is a wooden pole integrity testing (WPIT) system that autonomously assesses the integrity of wooden poles in real-time. The WPIT system includes a testing subsystem that is coupled to each wooden pole and that can, in real-time, non-invasively gather diagnostics indicative of the integrity of each wooden pole. The WPIT system can analyze the diagnostic data to determine a pole integrity of each wooden pole. Based on the integrity of a particular wooden pole, the WPIT system can schedule and preform preventive and predictive maintenance operations for that pole. The maintenance operations can include replacing the pole, repairing the pole, collecting further diagnostic data, determining that no operation needs to be performed, or other maintenance operations.

In some implementations, the WPIT system can periodically capture diagnostic data based on a pre-determined diagnostic cycle (for example, every three months, or other diagnostic cycle duration). Based on the diagnostic data, the WPIT system can predict a remaining lifetime of a wooden pole and can adjust the diagnostic cycle. For example, if a wooden pole has a short remaining lifetime (that is, the wooden pole is starting to significantly wear or decay), diagnostic data may need to be captured more frequently so that a fault or an abnormal condition can be detected early (that is, before a significant repair or replacement operation becomes necessary). In some implementations, when a fault or abnormal condition of the wooden pole is detected, an impact and severity of the fault or abnormal condition can be predicted, and a wooden pole replacement or repair can be scheduled and performed based on the predicted impact and severity.

In sum, the WPIT system provides a platform to perform diagnostic analysis for wooden poles in real-time and to autonomously schedule and perform proactive maintenance based on the analysis. For example, if a wooden pole is beginning to wear, a reduced diagnostic cycle duration can be automatically configured so that the pole can be more frequently monitored to prevent an accident. The proactive maintenance can increase reliability and stability of systems (for example, transmission systems) that use the wooden poles. The automated maintenance scheduling can increase operational efficiency and reduce effort of manual scheduling by an operator. Moreover, the automated maintenance scheduling capability enables workflow system integration, performance monitoring, and reporting on the site level, the field level, and even the enterprise level.

Figure 1:
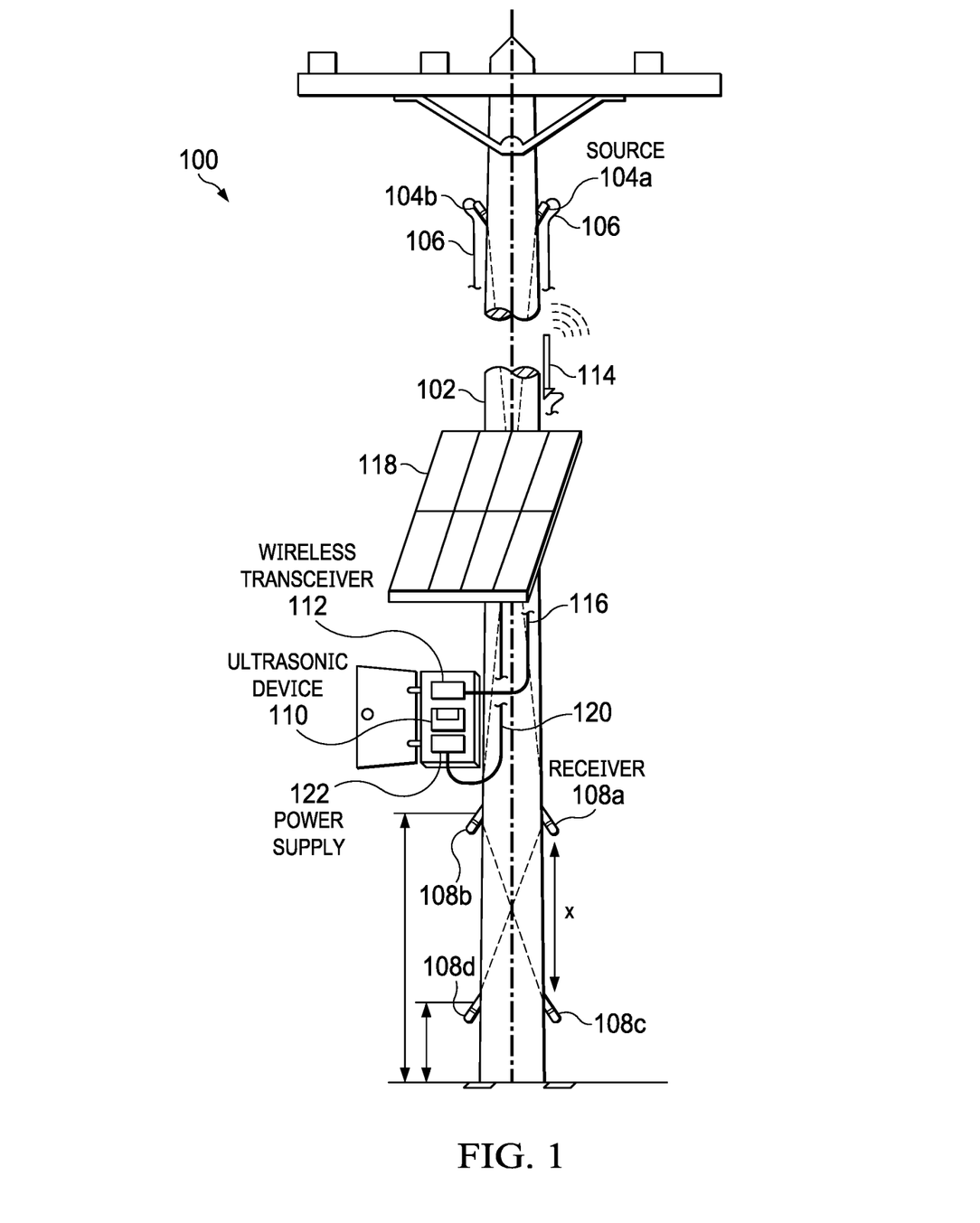
FIG. 1 illustrates an example non-invasive testing subsystem, according to some implementations.

FIG. 1 illustrates a non-invasive testing subsystem 100 coupled to a wooden pole 102, according to some implementations. The testing subsystem 100 is configured to non-invasively gather diagnostic data that could be used to determine a pole integrity ($P_I$) of the wooden pole 102. As explained herein, the testing subsystem 100 may be installed on one or more wooden poles operated by a transmission system operator. The testing subsystem 100 includes acoustic sources 104a, 104b, cable connectors 106, acoustic receivers 108a, 108b, 108c, and 108d, an acoustic ultrasonic device 110, a wireless transceiver 112, an antenna 114, an antenna cable 116, a solar panel 118, a power cable 120, and a power supply unit 122.

As shown in FIG. 1, the two acoustic sources 104a, 104b are mounted on opposite sides of a first end (for example, a top end) of the wooden pole 102. In an implementation, the acoustic sources 104a, 104b are ultrasonic excitation devices that generate ultrasonic signals. For example, the ultrasonic excitation devices are piezoelectric sound generators that have a rated voltage of 10-20 volts (V), a rated frequency of 22 kilohertz (kHz), and consume 5-20 watts (W) of power. The acoustic sources 104a, 104b are configured to non-invasively emit sound waves into the wooden pole 102 such that the sound waves travel through the wooden pole 102. For example, the acoustic sources 104a, 104b may emit ultrasonic sinusoidal sound waves that have a frequency greater than 20 kHz (for example, 22 kHz). As explained herein, the acoustic sources 104a, 104b emit the sound waves in order to collect the diagnostic data of the wooden pole 102.

The acoustic receivers 108a, 108b, 108c, and 108d may be coupled to the wooden pole 102 at a second end (for example, a bottom end) of the pole opposite to the first end. Two of the acoustic receivers may be coupled to one side of the wooden pole 102 and the other two receivers may be coupled to the other side. As shown in FIG. 1, the acoustic receivers 108a, 108c are coupled to one side of the wooden pole 102 and the acoustic receivers 108b, 108d are coupled to the other side. As also shown in FIG. 1, the two acoustic receivers on each side may be spaced by a length x. The acoustic receivers 108a, 108b, 108c, and 108d are configured to measure sound waves that are emitted into the wooden pole 102 by the acoustic sources 104a, 104b. In an implementation, the acoustic receivers 108a, 108b, 108c, and 108d are piezoelectric transducer devices that can detect sound waves of a particular frequency (for example, 22 kHz sound waves). The sound waves received at the acoustic receivers 108a, 108b, 108c, and 108d may be provided to the acoustic ultrasonic device 110.

The acoustic ultrasonic device 110 is configured to measure properties of the sound waves received at the acoustic receivers 108a, 108b, 108c, and 108d. In an example, the acoustic ultrasonic device 110 measures wave time delay in milliseconds (ms) and wave amplitude in millivolts (mV) of the sound waves. In particular, the wave time delay of a sound wave is the time between the wave being emitted by one of the acoustic sources 104a, 104b and the wave being received by one of the acoustic receivers 108a, 108b, 108c, and 108d. The measured wave time delay and wave amplitude make up the diagnostic data of the wooden pole 102.

The testing subsystem 100 may include a wireless communication system that facilitates communication with a central computing device of the WPIT system (not illustrated in FIG. 1). The testing subsystem 100 may receive instructions from the central computing device to collect diagnostic data of the wooden pole 1092. The testing system 100 may also provide the central computing device with the diagnostic data once the data is collected.

As shown in FIG. 1, the wireless communication system may include the wireless transceiver 112, the antenna 114, and the antenna cable 116. The wireless transceiver 112 is stored in an outdoor cabinet and is coupled to the antenna 114 (for example, a directional antenna) via the antenna cable 116. In an implementation, the wireless communication system is a Wi-Fi system that includes a Wi-Fi transceiver and a Wi-Fi antenna. Other types of wireless communication systems, such as WiMAX, are also possible. Additionally, the wireless communication system may include other devices not shown in FIG. 1, such as wireless repeaters that extend the range of the wireless communication system.

The testing subsystem 100 may also include a power system that supplies electrical energy to the testing subsystem 100. The power system includes the solar panel 118, the power cable 120, and the power supply unit 122. In an implementation, the solar panel 118 has an output of 150 W and 12 V-DC. The power supply unit 122 may be an AC/DC power supply that includes a backup battery unit (not illustrated in FIG. 1). As shown in FIG. 1, the solar panel 118 is coupled to the power supply unit 122 via the power cable 120 (for example, an insulated 300V power cable). Accordingly, the solar panel 118 can supply electrical energy to the power supply unit 122, which may then supply the energy to the testing subsystem 100 or may store the energy in the backup battery unit.

In an embodiment, the testing subsystem 100 is configured to non-invasively collect diagnostic data indicative of the $P_I$ of the wooden pole 102. In an implementation, the testing subsystem 100 collects the data by injecting acoustic signals at one end of the wooden pole 102 and measuring the acoustic signals at the other end of the pole. Generally, a degree of attenuation of acoustic signals traveling through the wooden pole 102 and a speed at which the signals travel through the pole are related to the $P_I$. More specifically, $P_I$ is inversely proportional to the degree of attenuation and directly proportional to the signal speed. Thus, the higher the degree of attenuation, the lower the pole integrity, and the faster the signal speed, the higher the pole integrity. For example, an acoustic signal traveling through a decayed wooden pole will be more attenuated and travel slower than an identical acoustic signal traveling through a new wooden pole.

In an implementation, the testing subsystem 100 collects data indicative of the $P_I$ of the wooden pole 102 by emitting, using the acoustic sources 104a, 104b, one or more sound waves into one end of the wooden pole 102 such that the sound waves travel along a length of the pole. In an example, the acoustic sources 104a, 104b emit sound waves at different timings and at different angles so that each sound wave travels along a different measurement path. In order to measure a degree of attenuation and speed of the sound waves, the testing subsystem 100 receives, at the acoustic receivers 108a, 108b, 108c, and 108d, at least a portion of the emitted one or more sound waves. The testing subsystem 100 then measures, using the acoustic ultrasonic device 110, an amplitude of the received one or more sound waves at each of the acoustic receivers 108a, 108b, 108c, and 108d. Additionally, the acoustic ultrasonic device 110 measures the time of arrival of the one or more sound waves at each of the acoustic receivers 108a, 108b, 108c, and 108d.

The testing subsystem 100 provides the sound wave data to the central computing device of the WPIT system that processes the data to determine the $P_I$ of the wooden pole 102. As explained above, $P_I$ is inversely proportional to the degree of attenuation of an acoustic signal and directly proportional to the signal speed. Equivalently, $P_I$ is directly proportional to the amplitude of the acoustic signal and inversely proportional to the arrival time of the acoustic signal. Thus, the higher the signal amplitude and the shorter the arrival time, the higher the $P_I$.

In an implementation, the central computing device calculates the $P_I$ by using a predetermined $P_I$ function. The input of the $P_I$ function is the sound wave data and the output is the $P_I$ of the wooden pole. In an example, the input is an average of the sound wave data that is measured by each receiver. Therefore, the function is a function of amplitude (a) and time of arrival (t) of a sound wave: $P_I=f(t, a)$. In an implementation, the predetermined function is generated by testing a response of a plurality of wooden poles with known pole integrities to one or more probing sound waves.

Figure 2:
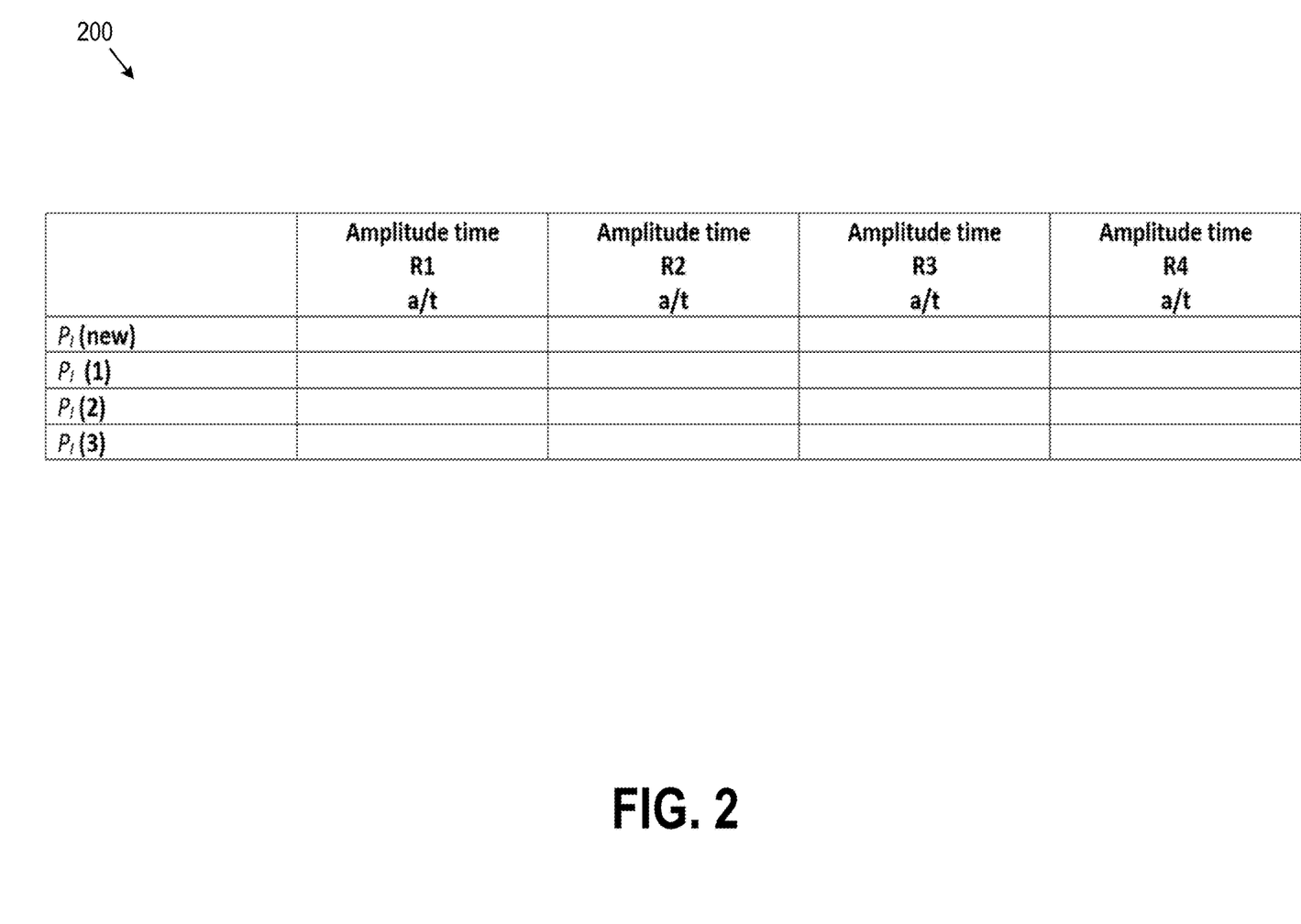
FIG. 2 illustrates an example table for generating a wooden pole integrity function, according to some implementations.

FIG. 2 illustrates an example table 200 for generating a wooden pole integrity function, according to some implementations. In an implementation, generating the $P_I$ function involves collecting sound wave data from a plurality of wooden poles of known pole integrities and developing an empirical correlation between sound wave data and pole integrities. In this implementation, a testing subsystem (for example, the testing subsystem 100) is installed on each of the plurality of wooden poles. In the example of FIG. 2, the sound wave data is collected from four wooden poles.

To collect the sound wave data, each subsystem causes a first acoustic source to emit a first sound wave and measures the amplitude and time of arrival of the first sound wave at the four receivers. Each subsystem then causes a second acoustic source to emit a second sound wave and measures the amplitude and time of arrival of the second sound wave at the four receivers. In an example, the second acoustic source is arranged at different angle than the first acoustic source so that the second sound wave travels along a different measurement path than the first sound wave. The sound wave data is tabulated in the table 200. In an example, the sound wave data of the first and second waves are used to calculate combined sound wave data for each receiver. For example, the time of arrival of the first and second wave for each receiver may be averaged in order to generate a single time of arrival for each receiver, and the sound wave amplitude of the first and second wave for each receiver may be averaged in order to generate a single value of amplitude for each receiver.

The $P_I$ function is then generated based on the sound wave data tabulated in the table 200. In an example, the function is generated using statistical techniques, such as regression analysis, that correlate the measured sound wave data to the known pole integrities of the plurality of poles. In an implementation, least squares regression analysis is used to correlate the measured sound wave data to the known pole integrities.

In another example, machine learning may be used to train a machine to develop the $P_I$ function. Generally, machine learning can encompass a wide variety of different techniques that are used to train a machine to perform specific tasks without being specifically programmed to perform those tasks. The machine can be trained using different machine learning techniques, including, for example, supervised learning, unsupervised learning, and reinforcement learning. In supervised learning, inputs and corresponding outputs of interest are provided to the machine. The machine adjusts its functions in order to provide the desired output when the inputs are provided. Supervised learning is generally used to teach a computer to solve problems in which are outcome determinative. In contrast, in unsupervised learning inputs are provided without providing a corresponding desired output. Unsupervised learning is generally used in classification problems such as, customer segmentation. Reinforcement learning describes an algorithm that a machine makes decisions using trial and error. Feedback informs the machine when a good choice or bad choice is made. The machine then adjusts its algorithms accordingly. During the training process, different algorithms may be used, including among others, generalized linear regression (GLM). A Poisson GLM is an algorithm used to model discrete counts based on independent inputs.

The generated $P_I$ function is used by the central computing device to calculate the $P_I$ for any wooden pole from which the central computing device receives diagnostic data.

Figure 3:
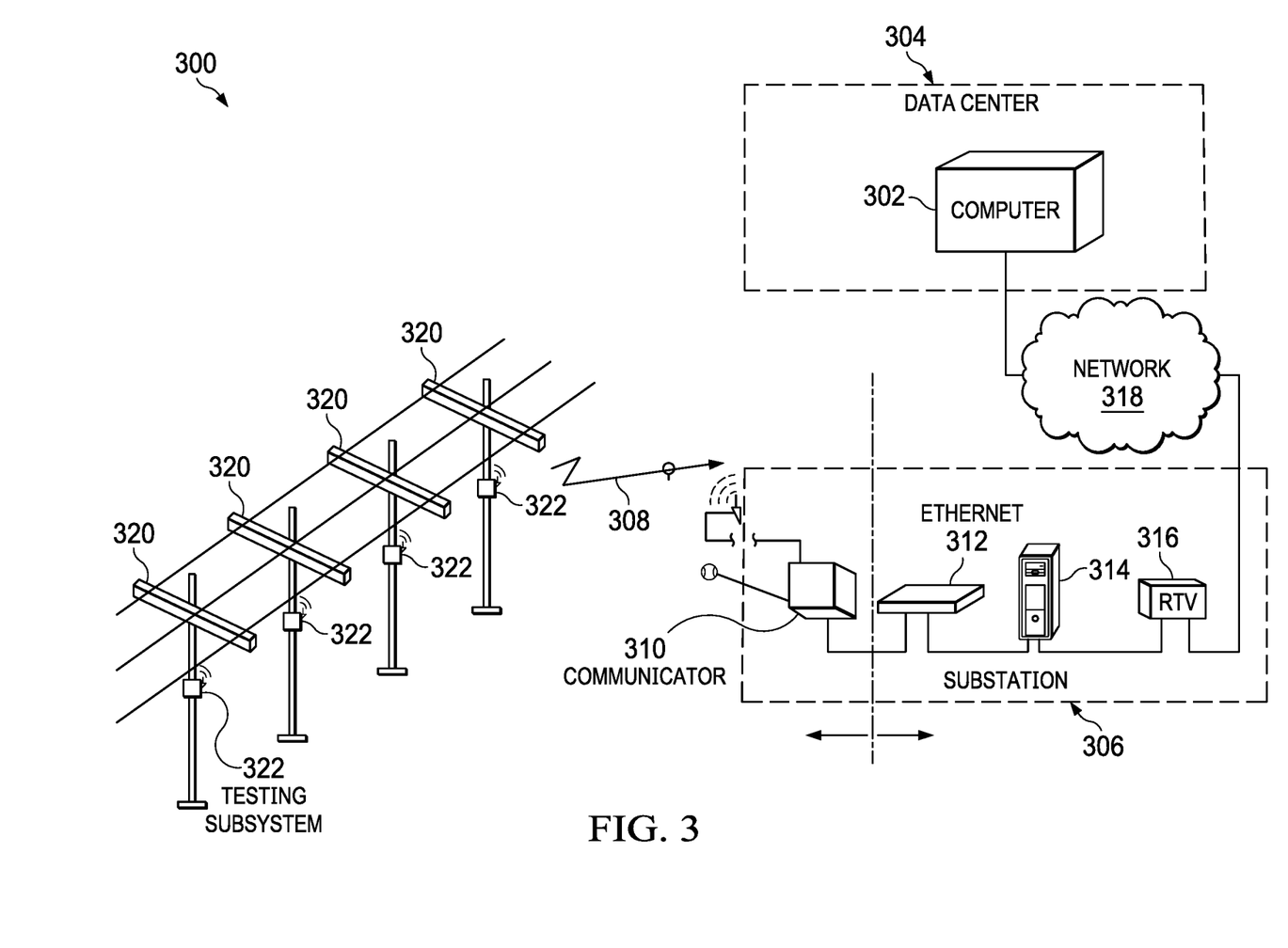
FIG. 3 illustrates an example wooden pole integrity testing system, according to some implementations.

FIG. 3 illustrates an example a wooden pole integrity testing (WPIT) system 300, according to some implementations. In this example, the WPIT system 300 is responsible for monitoring pole integrities of wooden poles 320 that are located in a remote area. In order to collect diagnostic data of the pole integrities, the WPIT system 300 includes a respective testing subsystem 322 coupled to each of the wooden poles 320. The WPIT system 300 also includes a central computing device 302, located in a data center 304, that is configured to communicate with the testing subsystems 322. For example, the central computing device 302 can provide the testing subsystems 322 with instructions and can receive diagnostic data from the testing subsystems 322. Because the wooden poles 320 are located in a remote location, the central computing device 302 communicates with the testing subsystems 322 through a supervisory control and data acquisition (SCADA) network located in a substation 306 that is located closer to the wooden poles 320 than the data center 304.

Generally, a SCADA network is a control system that uses computers, networked data communications, and graphical user interfaces for high-level process supervisory management. In this example, the SCADA network includes a SCADA server 314, a SCADA Ethernet Switch 312, and one or more remote terminal units (RTUs) 316. The SCADA server 314 can include operator interfaces that enable the monitoring and issuing of process commands. The RTU 316 is a microprocessor-controlled electronic device that interfaces objects in the physical world to the SCADA network by transmitting telemetry data to a master system, and by using messages from the SCADA network to control connected objects. The RTU 316 includes networked modules that perform real-time control logic or controller calculations. The RTU 316 can also be referred to as a remote telemetry unit or a remote telecontrol unit.

In order to facilitate communication between the central computing device 302 and the wooden poles 320, the SCADA network is communicatively coupled to both the central computing device 302 and the wooden poles 320. As shown in FIG. 3, the SCADA network communicates with the central computing device 304 via a network 318. The network 318 may be a wired or wireless communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses. As also shown in FIG. 3, the SCADA network communicates with the testing subsystems 322 via a wireless communication network 308. In particular, the SCADA network is coupled to a wireless communication device 310 that communicates via the wireless network 308 with wireless communication devices of the testing subsystems 322.

In an embodiment, the central computing device 302 periodically instructs the testing subsystems 322 to collect diagnostic data indicative of the pole integrities of the wooden poles 320. In some implementations, the diagnostic data of the wooden poles 320 can be periodically captured based on a pre-determined diagnostic cycle (for example, every three months or other cycle duration). In response to receiving instructions from the central computing device 302, the testing subsystems 322 collect the diagnostic data and provide the data to the computing device 302.

Once the central computing device 302 receives the diagnostic data, the central computing device processes the data to determine a respective $P_I$ for each wooden pole 320. In an example, the central computing device 302 determines the pole integrities by inputting the data into a $P_I$ function. In some implementations, the central computing device 302 can forecast a wooden pole heath based on the pole integrity of the wooden pole. For example, the central computing device 302 can forecast valve health and determine potential wooden pole failures over time based on a library of complex physical models developed under different conditions.

In some implementations, the central computing device 302, based on the $P_I$ of a wooden pole, can determine a reliability of the wooden pole that indicates a likelihood that the pole will not fail before a certain duration of time. In other words, the reliability indicates a probability that the remaining lifetime of the wooden pole is more than a certain duration of time. Typically, diagnostic data may need to be captured more frequently to avoid failure if the wooden pole is beginning to wear. For example, if normal maintenance occurs every three months, and the pole integrity is high, the 3-month normal maintenance cycle for capturing diagnostic data can be sufficient for the wooden pole. In some cases, if the wooden pole is in good condition, a maintenance cycle duration longer than the normal cycle duration can be used to reduce maintenance cost. However, if the pole integrity is low, an increased frequency of capturing diagnostic data, for example, once every month, may be needed. In some implementations, the diagnostic cycle may also be determined based on factors such as the age of the pole, the type of wood from which the pole is manufactured, and the diagnostic data associated with the pole. The central computing device 302 can dynamically schedule maintenance for each wooden pole based on individual health condition.

The central computing device 302 can detect faults and abnormal conditions in the wooden poles. Early detections of faults and abnormal conditions allow time to repair valves without unplanned shutdowns. After a fault or an abnormal condition has been detected, the central computing device 302 can send the information of the fault or abnormal condition to an operator of the wooden pole. For example, the central computing device 302 may output an alert on a display device of the central computing device 302 or another computing device. Additionally, the central computing device 302 can evaluate impact and severity of the detected fault and abnormal condition and can dynamically schedule maintenance based on the detected faults and abnormal conditions. For example, the central computing device 302 can define the schedule of capturing diagnostic data and performing diagnostic analysis to enable preventive and predictive maintenance. The central computing device 302 can also generate reports, actions, and alerts for manual intervention, for example, on a user interface to an operator.

Figure 4:
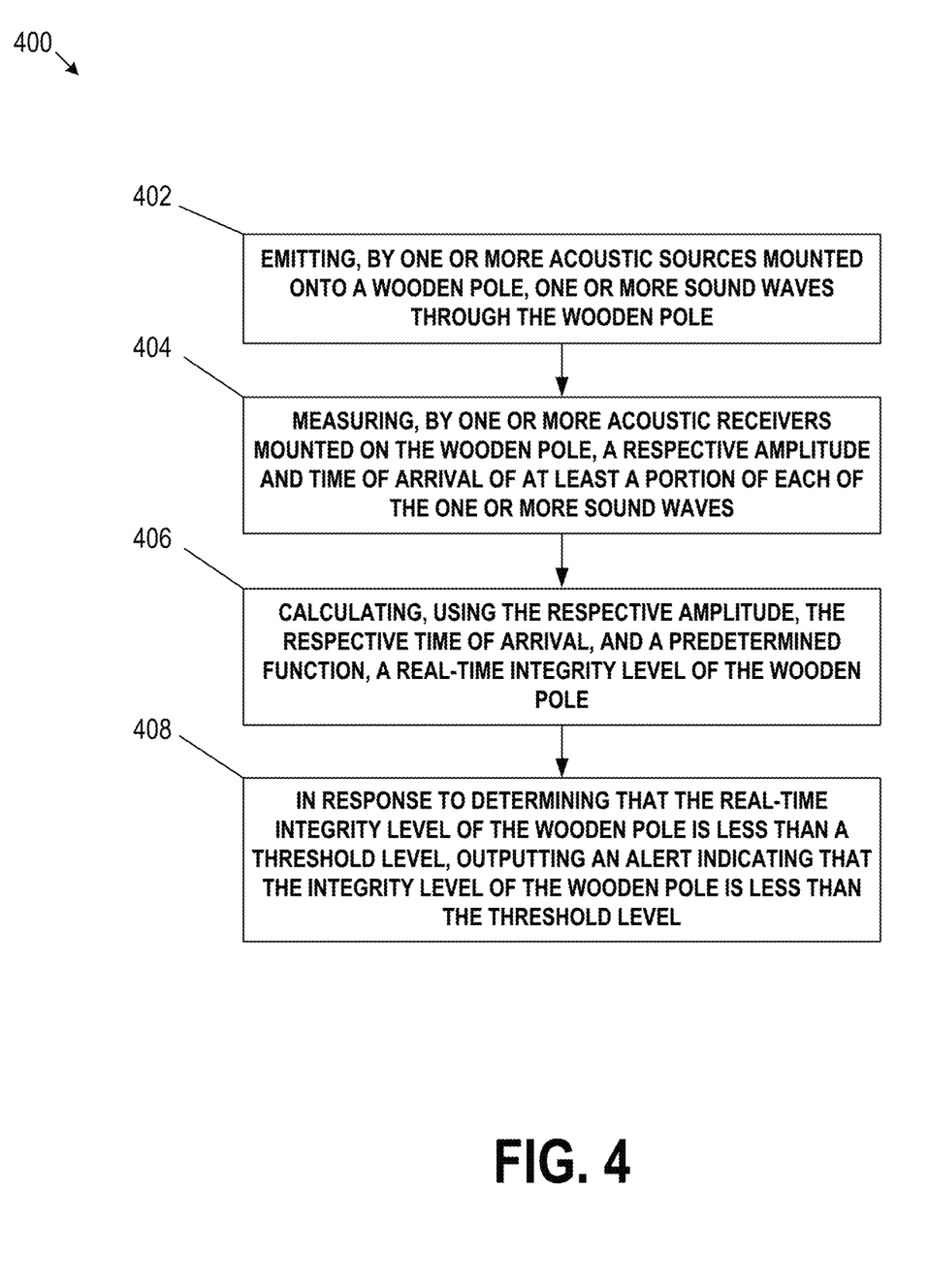
FIG. 4 is a flowchart illustrating an example method 400 for an automated assessment of an integrity of a wooden pole, according to some implementations, according to some implementations.

FIG. 4 is a flowchart illustrating an example method 400 for an automated assessment of an integrity of a wooden pole, according to some implementations. For clarity of presentation, the description that follows generally describes method 400 in the context of the other figures in this description. For example, method 400 can be performed by a computer system 500 described in FIG. 5. However, it will be understood that method 400 may be performed, for example, by any suitable system, environment, software, and hardware, or a combination of systems, environments, software, and hardware, as appropriate. In some implementations, various steps of method 400 can be run in parallel, in combination, in loops, or in any order.

The method 400 starts at step 402, which involves emitting, by one or more acoustic sources mounted onto a wooden pole, one or more sound waves through the wooden pole. In an embodiment, the wooden pole may be a utility pole that supports power distribution equipment, such as power distribution lines (for example, overhead power lines) and transformers. The utility pole may also support other equipment such as streetlights, traffic lights, and television/telephone/cable lines. In an example, each of the acoustic sources may be arranged at a different angle such that the respective sound waves emitted by each acoustic source travels along a different measurement path than the sound waves emitted by the other acoustic sources.

At step 404, the method 400 includes measuring, by one or more acoustic receivers mounted on the wooden pole, a respective amplitude and time of arrival of at least a portion of each of the one or more sound waves. The one or more acoustic receivers may be mounted on an opposite end to the end of the wooden pole on which the one or more acoustic sources are mounted.

At step 406, the method 400 includes calculating, using the respective amplitude, the respective time of arrival, and a predetermined function, a real-time integrity level of the wooden pole. In an implementation, the predetermined function is the pole integrity function described herein. The real-time integrity level of the wooden pole may be described on a predetermined scale, such as one a scale from 1-5, where 1 is the lowest integrity level and 5 is the highest integrity level. In an example, the time of arrival of each wave at each receiver may be averaged in order to generate a single time of arrival, and the sound wave amplitude of each wave at each receiver may be averaged in order to generate a single value of amplitude. The single value of time and the single value of amplitude may be provided as input to the predetermined function. The output of the predetermined function is an integrity of the wooden pole.

At step 408, the method 400 includes in response to determining that the real-time integrity level of the wooden pole is less than a threshold level, outputting an alert indicating that the integrity level of the wooden pole is less than the threshold level. For example, the threshold level is a level that indicates that the pole is significantly decayed and needs to be replaced.

The example method 400 shown in FIG. 4 can be modified or reconfigured to include additional, fewer, or different steps (not shown in FIG. 4), which can be performed in the order shown or in a different order.

In one aspect, the method 400 may further include periodically performing steps 402-408 to periodically determine the real-time integrity level of the wooden pole.

In another aspect, the one or more acoustic sources are ultrasonic excitation devices, the one or more sound waves are ultrasonic sound waves, and the one or more acoustic receivers are piezoelectric transducer devices.

In yet another aspect, the one or more sound waves are sinusoidal 22-kilohertz (kHz) waves.

In another aspect, the one or more acoustic sources and the one or more acoustic receivers are powered by a power supply unit comprising a solar panel.

In another aspect, the predetermined function is generated by: installing (i) respective first and second calibration acoustic sources, and (ii) respective calibration acoustic receivers on a plurality of calibration wooden poles. For each calibration wooden pole: emitting, by the respective first calibration acoustic source, a first calibration sound wave through the calibration wooden pole; measuring, by the respective acoustic receivers, an amplitude and an arrival time of the first calibration sound wave; emitting, by the respective second calibration acoustic source, a second calibration sound wave through the calibration wooden pole; and measuring, by the respective acoustic receivers, an amplitude and an arrival time of the second calibration sound wave. Based on (i) the amplitude and arrival time of the first calibration sound wave of each calibration wooden pole, (ii) the amplitude and arrival time of the second calibration sound wave of each calibration wooden pole, and (iii) a statistical model, generating the predetermined function to calculate a pole integrity based on arrival time and amplitude of sound waves.

In another aspect, the plurality of calibration wooden poles include a new wooden pole, where the plurality of calibration wooden poles other than the new wooden pole are pre-damaged wooden poles with known respective pole integrities.

In another aspect, the statistical model is least square regression.

In some implementations, one or more of the steps shown in FIG. 4 can be repeated or reiterated, for example, until a terminating condition is reached. In some implementations, one or more of the individual steps shown in FIG. 4 can be executed as multiple separate steps, or one or more subsets of the steps shown in FIG. 4 can be combined and executed as a single step. In some implementations, one or more of the individual steps shown in FIG. 4 may also be omitted from the example method 400.

Figure 5:
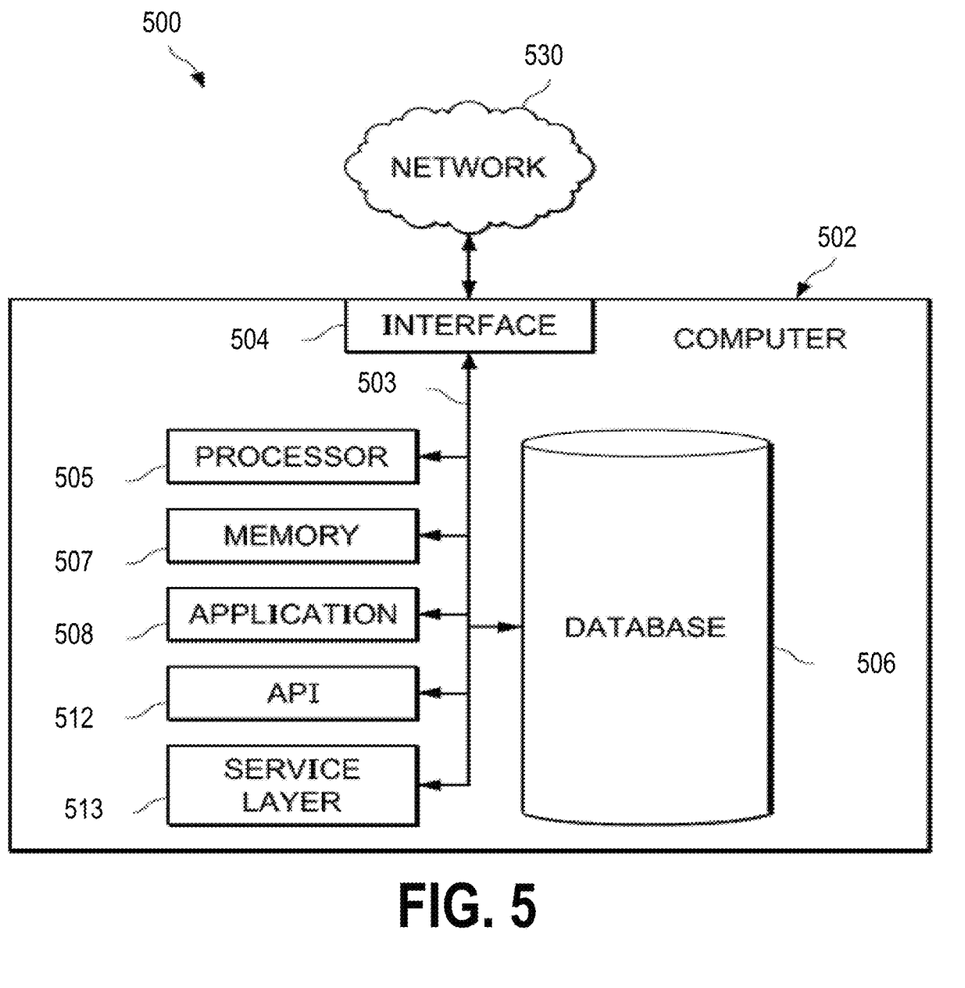
FIG. 5 illustrates a block diagram of an example computer system used to provide computational functionalities associated with described algorithms, methods, functions, processes, flows, and procedures as described in the instant disclosure, according to some implementations.

FIG. 5 is a block diagram of an example computer system 500 used to provide computational functionalities associated with described algorithms, methods, functions, processes, flows, and procedures as described in the instant disclosure, according to an implementation. The illustrated computer 502 is intended to encompass any computing device such as a server, desktop computer, laptop/notebook computer, wireless data port, smart phone, personal data assistant (PDA), tablet computing device, or one or more processors within these devices, or any other suitable processing device, including physical or virtual instances (or both) of the computing device. Additionally, the computer 502 may comprise a computer that includes an input device, such as a keypad, keyboard, or touch screen, or other device that can accept user information, and an output device that conveys information associated with the operation of the computer 502, including digital data, visual, or audio information (or a combination of information), or a graphical user interface (GUI).

The computer 502 can serve in a role as a client, network component, a server, a database or other persistency, or any other component (or a combination of roles) of a computer system for performing the subject matter described in the instant disclosure. The illustrated computer 502 is communicably coupled with a network 530. In some implementations, one or more components of the computer 502 may be configured to operate within environments, including cloud-computing-based, local, or global, or other environment (or a combination of environments).

At a high level, the computer 502 is an electronic computing device operable to receive, transmit, process, store, or manage data and information associated with the described subject matter. According to some implementations, the computer 502 may also include or be communicably coupled with an application server, e-mail server, web server, caching server, or streaming data server, or other server (or a combination of servers).

The computer 502 can receive requests over network 530 from a client application (for example, executing on another computer) and respond to the received requests by processing the received requests using the appropriate software application(s). In addition, requests may also be sent to the computer 502 from internal users (for example, from a command console or by other appropriate access methods), external or third-parties, other automated applications, as well as any other appropriate entities, individuals, systems, or computers.

Each of the components of the computer 502 can communicate using a system bus 503. In some implementations, any or all of the components of the computer 502, both hardware or software (or a combination of hardware and software), may interface with each other or the interface 504 (or a combination of both) over the system bus 503 using an application programming interface (API) 512 or a service layer 513 (or a combination of the API 512 and service layer 513). The API 512 may include specifications for routines, data structures, and object classes. The API 512 may be either computer-language independent or dependent and may refer to a complete interface, a single function, or even a set of APIs. The service layer 513 provides software services to the computer 502 or other components (whether or not illustrated) that are communicably coupled to the computer 502. The functionality of the computer 502 may be accessible for all service consumers using this service layer. Software services, such as those provided by the service layer 513, provide reusable, defined functionalities through a defined interface. For example, the interface may be software written in JAVA, or C++, or other suitable language providing data in extensible markup language (XML) format or other suitable format. While illustrated as an integrated component of the computer 502, alternative implementations may illustrate the API 512 or the service layer 513 as stand-alone components in relation to other components of the computer 502 or other components (whether or not illustrated) that are communicably coupled to the computer 502. Moreover, any or all parts of the API 512 or the service layer 513 may be implemented as child or sub-modules of another software module, enterprise application, or hardware module, without departing from the scope of this disclosure.

The computer 502 includes an interface 504. Although illustrated as a single interface 504 in FIG. 5, two or more interfaces 504 may be used according to particular needs, desires, or particular implementations of the computer 502. The interface 504 is used by the computer 502 for communicating with other systems that are connected to the network 530 (whether illustrated or not) in a distributed environment. Generally, the interface 504 comprises logic encoded in software or hardware (or a combination of software and hardware) and is operable to communicate with the network 530. More specifically, the interface 504 may comprise software supporting one or more communication protocols associated with communications such that the network 530 or interface's hardware is operable to communicate physical signals within and outside of the illustrated computer 502.

The computer 502 includes a processor 505. Although illustrated as a single processor 505 in FIG. 5, two or more processors may be used according to particular needs, desires, or particular implementations of the computer 502. Generally, the processor 505 executes instructions and manipulates data to perform the operations of the computer 502 and any algorithms, methods, functions, processes, flows, and procedures as described in the instant disclosure.

The computer 502 also includes a database 506 that can hold data for the computer 502 or other components (or a combination of both) that can be connected to the network 530 (whether illustrated or not). For example, database 506 can be an in-memory, or conventional, or other type of database storing data consistent with this disclosure. In some implementations, database 506 can be a combination of two or more different database types (for example, a hybrid in-memory and conventional database) according to particular needs, desires, or particular implementations of the computer 502 and the described functionality. Although illustrated as a single database 506 in FIG. 5, two or more databases (of the same or combination of types) can be used according to particular needs, desires, or particular implementations of the computer 502 and the described functionality. While database 506 is illustrated as an integral component of the computer 502, in alternative implementations, database 506 can be external to the computer 502.

The computer 502 also includes a memory 507 that can hold data for the computer 502 or other components (or a combination of both) that can be connected to the network 530 (whether illustrated or not). For example, memory 507 can be random access memory (RAM), read-only memory (ROM), optical, magnetic, and the like, storing data consistent with this disclosure. In some implementations, memory 507 can be a combination of two or more different types of memory (for example, a combination of RAM and magnetic storage) according to particular needs, desires, or particular implementations of the computer 502 and the described functionality. Although illustrated as a single memory 507 in FIG. 5, two or more memories 507 (of the same or a combination of types) can be used according to particular needs, desires, or particular implementations of the computer 502 and the described functionality. While memory 507 is illustrated as an integral component of the computer 502, in alternative implementations, memory 507 can be external to the computer 502.

The application 508 is an algorithmic software engine providing functionality according to particular needs, desires, or particular implementations of the computer 502, particularly with respect to functionality described in this disclosure. For example, application 508 can serve as one or more components, modules, or applications. Further, although illustrated as a single application 508, the application 508 may be implemented as multiple applications 508 on the computer 502. In addition, although illustrated as integral to the computer 502, in alternative implementations, the application 508 can be external to the computer 502.

There may be any number of computers 502 associated with, or external to, a computer system containing computer 502, each computer 502 communicating over network 530. Further, the term "client", "user", and other appropriate terminology may be used interchangeably, as appropriate, without departing from the scope of this disclosure. Moreover, this disclosure contemplates that many users may use one computer 502, or that one user may use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS, or any other suitable conventional operating system.

A computer program, which may also be referred to or be described as a program, software, a software application, a module, a software module, a script, or code can be written in any form of programming language, including compiled or interpreted languages, or declarative or procedural languages, and it can be deployed in any form, including as a stand-alone program or as a module, component, or subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, or methods, or other processes, the programs may instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a ROM or a RAM, or both. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, such as, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11a/b/g/n or 802.20 (or a combination of 802.11x and 802.20, or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, or in a single implementation. Conversely, various features that are described in the context of a single implementation can also be implemented in multiple implementations, separately, or in any suitable sub-combination. Moreover, although previously-described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously-described implementations should not be understood as requiring such separation or integration in all implementations, and it should be understood that the described program components and systems can generally be integrated together in a single software product or packaged into multiple software products.

Accordingly, the previously-described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

The invention claimed is:

1. A method for remotely determining a real-time integrity of a plurality of wooden poles, the method comprising:
    generating, by a central computing device and based on an inspection cycle for a first wooden pole of the plurality, instructions for determining a real-time integrity level for the first wooden pole;
    sending, by the central computing device, the instructions to a supervisory control and data acquisition (SCADA) network, wherein the SCADA network is located closer to the plurality of wooden poles than the central computing device;
    sending, by the SCADA network, the instructions to a testing system mounted onto the first wooden pole;
    in response to receiving the instructions, emitting, by one or more acoustic sources of the testing system, one or more sound waves through the first wooden pole;
    measuring, by one or more acoustic receivers of the testing system, a respective amplitude and respective time of arrival of at least a portion of each of the one or more sound waves, wherein the one or more acoustic receivers are vertically displaced from the one or more acoustic sources;
    sending, by the testing system and via the SCADA network, the respective amplitude and respective time of arrival to the central computing device;
    calculating, by the central computing device and using the respective amplitude, the respective time of arrival, and a predetermined function, the real-time integrity level of the first wooden pole; and
    in response to determining that the real-time integrity level of the first wooden pole is less than a threshold, causing, by the central computing device, output of an alert.

2. The method of claim 1, wherein the one or more acoustic sources are ultrasonic excitation devices, the one or more sound waves are ultrasonic sound waves, and the one or more acoustic receivers are piezoelectric transducer devices.

3. The method of claim 1, wherein the one or more sound waves are sinusoidal 22-kilohertz (kHz) waves.

4. The method of claim 1, wherein the one or more acoustic sources and the one or more acoustic receivers are powered by a power supply unit comprising a solar panel.

5. The method of claim 1, wherein the predetermined function is generated by:
    installing (i) respective first and second calibration acoustic sources, and (ii) respective calibration acoustic receivers on a plurality of calibration wooden poles;
    for each calibration wooden pole:
        emitting, by the respective first calibration acoustic source, a first calibration sound wave through the calibration wooden pole;
        measuring, by the respective acoustic receivers, an amplitude and an arrival time of the first calibration sound wave;
        emitting, by the respective second calibration acoustic source, a second calibration sound wave through the calibration wooden pole; and
        measuring, by the respective acoustic receivers, an amplitude and an arrival time of the second calibration sound wave; and
    based on (i) the amplitude and arrival time of the first calibration sound wave of each calibration wooden pole, (ii) the amplitude and arrival time of the second calibration sound wave of each calibration wooden pole, and (iii) a statistical model, generating the predetermined function to calculate a pole integrity based on arrival time and amplitude of sound waves.

6. The method of claim 5, wherein the plurality of calibration wooden poles comprise a new wooden pole, and wherein the plurality of calibration wooden poles other than the new wooden pole are pre-damaged wooden poles with known respective pole integrities.

7. The method of claim 5, wherein the statistical model is least square regression.

8. A system for remotely determining a real-time integrity of a plurality of wooden poles, the system comprising:
    a central computing device;
    a supervisory control and data acquisition (SCADA) network communicatively coupled to the central computing device; and
    a plurality of testing systems mounted on the plurality of wooden poles, wherein the plurality of testing systems are communicatively coupled to the SCADA network, and wherein a first testing system is mounted on a first wooden pole, the first testing system comprising;
        one or more acoustic sources;
        one or more acoustic receivers vertically displaced from the one or more acoustic sources;
        a memory; and
        a processing unit that is arranged to perform operations including:
            receiving, from the central computing device and via the SCADA network, instructions for determining a real-time integrity level for the first wooden pole, wherein the instructions are generated by the central computing device based on an inspection cycle for testing an integrity of the first wooden pole;
            emitting, by the one or more acoustic sources, one or more sound waves through the first wooden pole;
            measuring, by the one or more acoustic receivers, a respective amplitude and respective time of arrival of at least a portion of each of the one or more sound waves; and
            sending, via the SCADA network, the respective amplitude and time of arrival to the central computing device, wherein the central computing device is configured to: (i) calculate, using the respective amplitude, the respective time of arrival, and a predetermined function, a real-time integrity level of the first wooden pole, and (ii) in response to determining that the real-time integrity level is less than a threshold, cause output of an alert.

9. The system of claim 8, wherein the central computing device is configured to periodically send instructions to the plurality of testing systems to determine the real-time integrity of the plurality of wooden poles.

10. The system of claim 8, wherein the one or more acoustic sources are ultrasonic excitation devices, the one or more sound waves are ultrasonic sound waves, and the one or more acoustic receivers are piezoelectric transducer devices.

11. The system of claim 8, wherein the one or more sound waves are sinusoidal 22-kilohertz (kHz) waves.

12. The system of claim 8, wherein the one or more acoustic sources and the one or more acoustic receivers are powered by a power supply unit comprising a solar panel.

13. The system of claim 8, wherein the predetermined function is generated by:
   installing (i) respective first and second calibration acoustic sources, and (ii) respective calibration acoustic receivers on a plurality of calibration wooden poles;
   for each calibration wooden pole:
      emitting, by the respective first calibration acoustic source, a first calibration sound wave through the calibration wooden pole;
      measuring, by the respective acoustic receivers, an amplitude and an arrival time of the first calibration sound wave;
      emitting, by the respective second calibration acoustic source, a second calibration sound wave through the calibration wooden pole; and
      measuring, by the respective acoustic receivers, an amplitude and an arrival time of the second calibration sound wave; and
   based on (i) the amplitude and arrival time of the first calibration sound wave of each calibration wooden pole, (ii) the amplitude and arrival time of the second calibration sound wave of each calibration wooden pole, and (iii) a statistical model, generating the predetermined function to calculate a pole integrity based on arrival time and amplitude of sound waves.

14. The system of claim 13, wherein the plurality of calibration wooden poles comprise a new wooden pole, and wherein the plurality of calibration wooden poles other than the new wooden pole are pre-damaged wooden poles with known respective pole integrities.

15. A non-transitory computer-readable medium storing instructions executable by a computer system to perform operations for remotely determining a real-time integrity of a plurality of wooden poles, the operations comprising:

generating, by a central computing device and based on an inspection cycle for a first wooden pole of the plurality, instructions for determining a real-time integrity level for the first wooden pole;
   sending, by the central computing device, the instructions to a supervisory control and data acquisition (SCADA) network, wherein the SCADA network is located closer to the plurality of wooden poles than the central computing device;
   sending, by the SCADA network, the instructions to a testing system mounted onto the first wooden pole;
   in response to receiving the instructions, emitting, by one or more acoustic sources of the testing system, one or more sound waves through the first wooden pole;
   measuring, by one or more acoustic receivers of the testing system vertically displaced from the one or more acoustic sources, a respective amplitude and respective time of arrival of at least a portion of each of the one or more sound waves;
   sending, by the testing system and via the SCADA network, the respective amplitude and respective time of arrival to the central computing device;
   calculating, by the central computing device and using the respective amplitude, the respective time of arrival, and a predetermined function, the real-time integrity level of the first wooden pole; and
   in response to determining that the real-time integrity level of the first wooden pole is less than a threshold level, causing, by the central computing device, output of an alert.

16. The non-transitory computer-readable medium of claim 15, wherein the one or more acoustic sources are ultrasonic excitation devices, the one or more sound waves are ultrasonic sound waves, and the one or more acoustic receivers are piezoelectric transducer devices.

17. The non-transitory computer-readable medium of claim 15, wherein the one or more sound waves are sinusoidal 22-kilohertz (kHz) waves.

18. The non-transitory computer-readable medium of claim 15, wherein the one or more acoustic sources and the one or more acoustic receivers are powered by a power supply unit comprising a solar panel.

\* \* \* \* \*

UNITED STATES PATENT AND TRADEMARK OFFICE
CERTIFICATE OF CORRECTION

PATENT NO. : 11,079,358 B2  
APPLICATION NO. : 16/394553  
DATED : August 3, 2021  
INVENTOR(S) : Khaled A. Al-Buraik Page 1 of 1

It is certified that error appears in the above-identified patent and that said Letters Patent is hereby corrected as shown below:

In the Claims

Column 20, Lines 29-30 (approx.), Claim 15, delete "threshold level," and insert -- threshold, --.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*